(12) United States Patent
Doerr et al.

(10) Patent No.: US 9,827,429 B2
(45) Date of Patent: Nov. 28, 2017

(54) MEDICAL IMPLANT WITH CONTACT PORTIONS THAT CONVERTS MOVEMENT FROM THE CONTACT PORTIONS INTO AN ELECTRICAL SIGNAL

(71) Applicant: Biotronik SE & Co. KG, Berlin (DE)

(72) Inventors: Thomas Doerr, Berlin (DE); Michael Diebold, Berlin (DE)

(73) Assignee: Biotronik SE & Co. KG, Berlin (DE)

( * ) Notice: Subject to any disclaimer, the term of this patent is extended or adjusted under 35 U.S.C. 154(b) by 95 days.

(21) Appl. No.: 14/802,964

(22) Filed: Jul. 17, 2015

(65) Prior Publication Data

US 2016/0051824 A1 Feb. 25, 2016

Related U.S. Application Data

(60) Provisional application No. 62/038,847, filed on Aug. 19, 2014.

(51) Int. Cl.
*A61N 1/378* (2006.01)
*A61B 5/00* (2006.01)
(Continued)

(52) U.S. Cl.
CPC .............. *A61N 1/3785* (2013.01); *A61B 5/07* (2013.01); *A61B 5/6869* (2013.01); *A61B 5/6882* (2013.01); *A61N 1/025* (2013.01); *A61N 1/059* (2013.01); *A61N 1/0587* (2013.01); *A61N 1/362* (2013.01); *A61B 2560/0214* (2013.01); *A61N 1/0573* (2013.01); *A61N 1/375* (2013.01); *H02N 2/18* (2013.01)

(58) Field of Classification Search
CPC .... A61N 1/3785; A61N 1/025; A61N 1/0587; A61N 1/059; A61N 1/362; A61N 1/0573; A61N 1/375; A61B 5/07; A61B 5/6869; A61B 5/6882; A61B 2560/0214; H02N 2/18
USPC .................................................. 607/2, 9, 35
See application file for complete search history.

(56) References Cited

U.S. PATENT DOCUMENTS

2005/0055061 A1 3/2005 Holzer
2008/0262562 A1* 10/2008 Roberts ................ H02K 7/1876
607/35

(Continued)

FOREIGN PATENT DOCUMENTS

DE 102004043002 A1 3/2006
WO 2007068284 A1 6/2007
WO 2012020034 A1 2/2012

OTHER PUBLICATIONS

European Search Report received from EP Application Serial No. 15168077, dated Jan. 5, 2016, 6 pages.

*Primary Examiner* — Michael Carey
(74) *Attorney, Agent, or Firm* — ARC IP LAW, PC; Joseph J. Mayo

(57) ABSTRACT

A medical implant including an implant body for insertion into a human and/or animal body. The implant body includes at least one first and at least one second contact portion, wherein the at least one first and the at least one second contact portions contact two tissue regions performing a relative movement with respect to one another. The at least one first and the at least one second contact portions are movable relative to one another, wherein a relative movement of the contact portions may be converted into an electrical signal.

12 Claims, 4 Drawing Sheets

(51) Int. Cl.
    *A61N 1/02*     (2006.01)
    *A61N 1/362*     (2006.01)
    *A61B 5/07*     (2006.01)
    A61N 1/375     (2006.01)
    A61N 1/05     (2006.01)
    H02N 2/18     (2006.01)

(56) References Cited

U.S. PATENT DOCUMENTS

| | | | |
|---|---|---|---|
| 2009/0152990 A1* | 6/2009 | Brown | F03G 5/06 310/339 |
| 2009/0171408 A1 | 7/2009 | Solem | |
| 2009/0216292 A1* | 8/2009 | Pless | A61N 1/3785 607/33 |
| 2011/0275947 A1 | 11/2011 | Feldman et al. | |

* cited by examiner

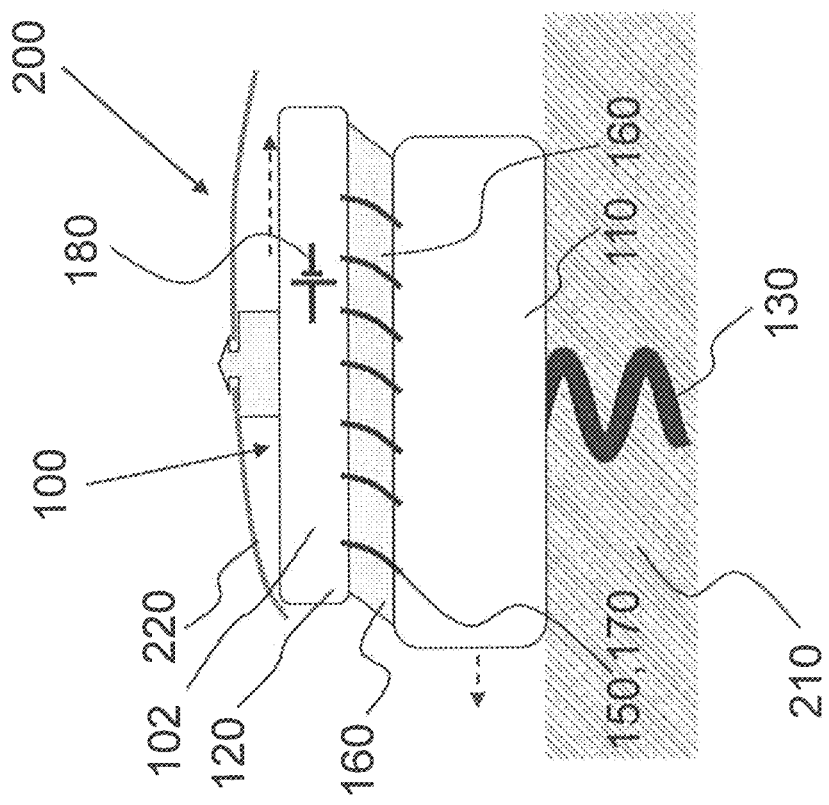
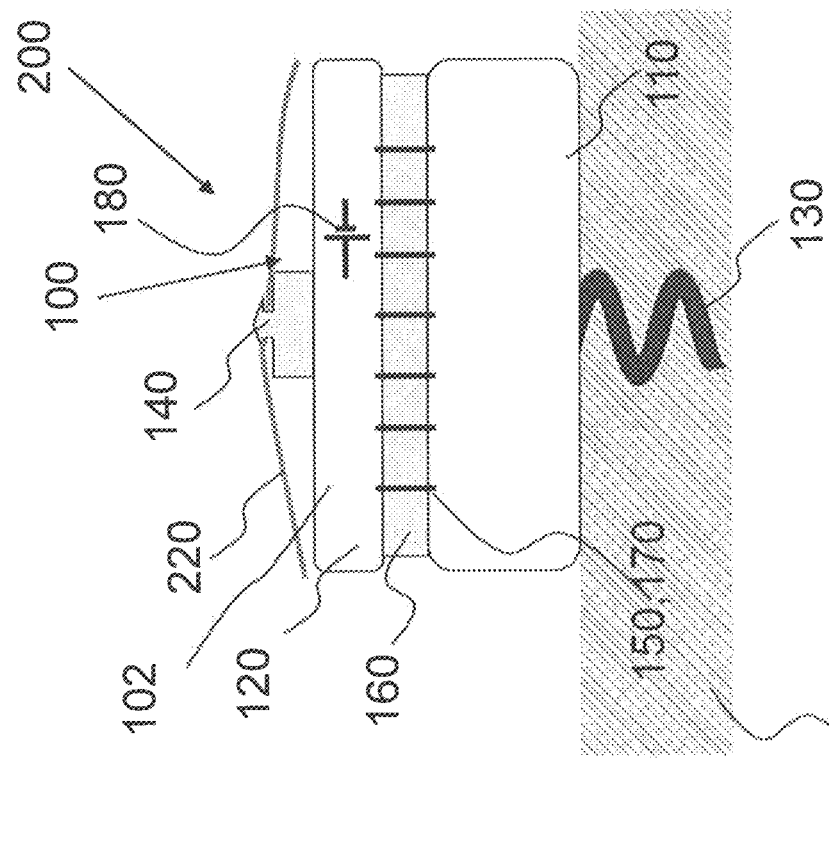

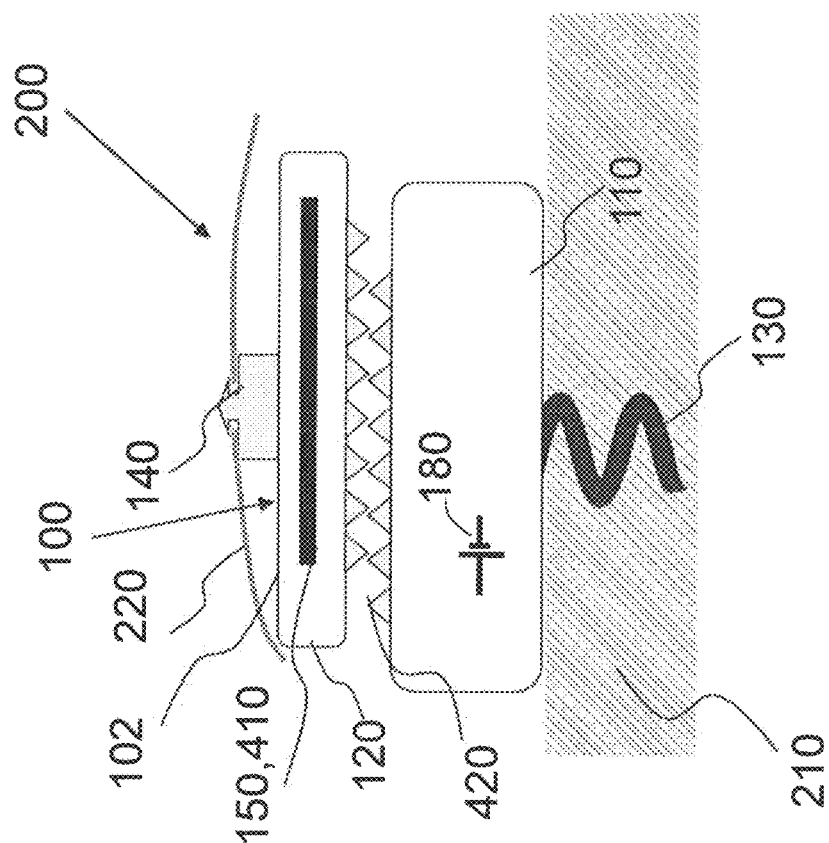
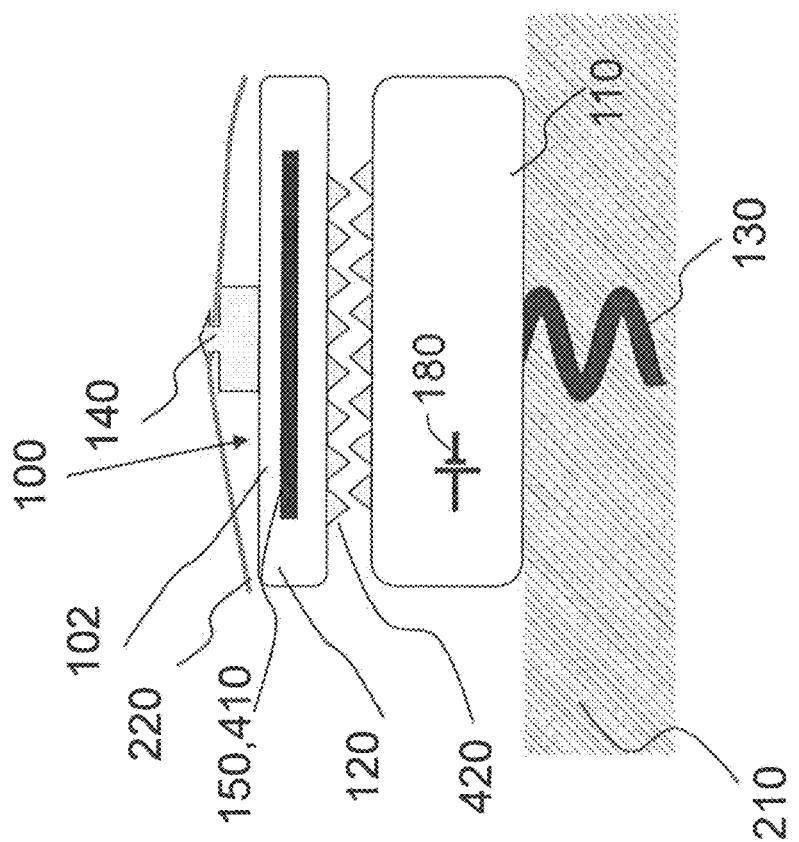
Fig. 7
Fig. 6

MEDICAL IMPLANT WITH CONTACT PORTIONS THAT CONVERTS MOVEMENT FROM THE CONTACT PORTIONS INTO AN ELECTRICAL SIGNAL

This application claims the benefit of U.S. Provisional Patent Application 62/038,847 filed on 19 Aug. 2014, the specification of which is hereby incorporated herein by reference.

BACKGROUND OF THE INVENTION

Field of the Invention

Embodiments of the invention generally relate to a medical implant for insertion into the human and/or animal body.

Description of the Related Art

Generally, medical implants for insertion into the human and/or animal body are known. Typically, implants of this type may have a self-sufficient power supply, which draws energy from the body into which these implants have been inserted. Generally, this is also known as "energy harvesting". Typically, the level of efficacy is low and the amount of energy obtained is therefore often insufficient. Generally, this is particularly the case with implants with therapeutic energy delivery, which have an increased energy demand.

BRIEF SUMMARY OF THE INVENTION

One or more embodiments of the invention include an electronic implant that has an increased level of efficacy.

One or more embodiments of the invention are achieved in accordance with elements of the independent claims. Embodiments of the invention will emerge from the rest of the claims, the description and the drawings presented herein.

At least one embodiment of the invention includes a medical implant that is inserted into the human and/or animal body. In one or more embodiments, the medical implant includes an implant body, wherein the implant body may include at least one first and at least one second contact portion. In at least one embodiment, the contact portions may contact two tissue regions performing a relative movement with respect to one another, wherein the first and second contact portions are movable relative to one another, and wherein a relative movement of the contact portions may be converted into an electrical signal.

One or more embodiments of the invention provide autonomous power supply of electronic implants, wherein the electronic implants are secured during the intended use between two body tissue portions that exert a more or less cyclical movement relative to one another. At least one embodiment of the invention may be used for all active implants that are implanted between body tissues that have a repeated, in particular continuous, movement relative to one another. In one or more embodiments, the movement energy of the tissue may be transformed into electrical energy via the contact portions connected to the tissue. At least one embodiment of the invention provides a very compact design and a good coupling of the tissue movement, wherein an improvement of the level of efficacy may be achieved. One or more embodiments of the invention may be suitable with permanently implantable electronic implants to provide diagnostics and/or therapy.

In at least one embodiment, the first and/or the second contact portion may be coupled directly or indirectly to an electric generator in or on the implant body. According to one or more embodiments, a direct coupling corresponds to a mechanical connection to a movable part of a generator, for example a coil or a magnet electromagnetically operatively connected to the coil.

In at least one embodiment, the first contact portion may include a fixing element to fasten the implant body to one of the tissue regions. For example, in one or more embodiments, the fixing element may be a fixing helix. In at least one embodiment, an adhesive bond may be provided between the implant housing and tissue region.

In at least one embodiment, the first and/or second contact portion may be mechanically connected to a movable element of the generator. As such, in one or more embodiments, the contact region may be connected to the coil of a generator or to the magnet of the generator. In at least one embodiment, a movement of the contact portion may induce an electric voltage via the electromagnetic operative connection between coil and magnet.

In at least one embodiment, the implant body may be formed in, or include, a number of parts, wherein at least two parts may be movable relative to one another, and wherein each of the parts of the implant body is associated with a contact portion. In one or more embodiments, the parts may be coupled using at least one piezoelectric element. In at least one embodiment, a mechanical oscillation generator may be arranged between parts of the implant body, at least in some regions. Due to the relative movement of the tissue, by way of one or more embodiments, the parts of the implant body may be moved relative to one another via the contact portions, wherein the kinetic energy of the tissue movement is diverted into the implant body and may be converted.

In at least one embodiment, the generator may be an electrostatic generator, which may be driven via mechanical waves. In one or more embodiments, a micromechanical electrostatic generator may be used. In at least one embodiment, a mechanical structure may be provided between the parts of the multi-part implant body, such that mechanical oscillations are produced by the tissue movement and are adjusted in terms of frequency and mode of oscillation to the electrostatic generator. As such, in one or more embodiments, the mechanical structure may be operated as close to resonance as possible.

In at least one embodiment, the second contact device may be a fixing element to fasten the implant body to one of the tissue regions. As such, in one or more embodiments, particularly effective coupling of the relative movement of the tissue regions into the implant is possible.

At least one embodiment of the invention may include an energy store provided in the implant body. In one or more embodiments, the energy store may be an accumulator, a capacitor or a mechanical flywheel store. As such, in at least one embodiment, generated electrical energy may be stored and used selectively for diagnostics and/or for therapeutic energy delivery from the implant into the tissue. In one or more embodiments, the mechanical flywheel store may be used for short-term energy storage, wherein a conversion of the movement energy into a rotation energy is performed. In at least one embodiment, the rotation energy is only converted into an electrical energy as necessary, for example by electric loading of a generator.

At least one embodiment may include a control and/or regulation unit provided in the implant body or may be coupled thereto in order to selectively induce a therapeutic energy delivery. Such a control and/or regulation unit, in one or more embodiments, may include an electronic circuit which initiates or stops or varies the corresponding therapy in accordance with the therapeutic demand, for example a timer in a cardiac pacemaker.

In at least one embodiment, the implant may be formed as, or include, an epicardial pacemaker. Such a pacemaker, in one or more embodiments, may be inserted between the myocardium and pericardium and may use the strong relative movement between the myocardium and pericardium effectively to recover energy.

In at least one embodiment, the implant may be arranged in other tissue regions that experience a constant movement, such as the lung-diaphragm region, muscular tissue transitions, vertebra transitions and bone transitions.

One or more embodiments of the invention allow the level of efficacy of the energy recovery in electronic implants by conversion of mechanical body movements into electrical energy to be increased considerably compared with typical implants.

BRIEF DESCRIPTION OF THE DRAWINGS

The above and other aspects, features and advantages of at least one embodiment of the invention will be more apparent from the following more particular description thereof, presented in conjunction with the following drawings, wherein:

FIG. 4 schematically shows a section through an implantation area with an epicardial implant divided into two in a first position in accordance with an exemplary embodiment of the invention, wherein a first part of the implant is fixed via a first contact portion in the form of a fixing helix in a first tissue region and a second part of the implant is fixed via a second contact portion at a further tissue region, wherein the implant parts are connected to piezoelectric elements;

FIG. 5 schematically shows the implant of FIG. 4 in a deflected position;

FIG. 6 schematically shows a section through an implantation area with an epicardial implant divided into two in a first position in accordance with an exemplary embodiment of the invention, wherein a first part of the implant is fixed via a first contact portion in the form of a fixing helix in a first tissue region and a second part of the implant is fixed via a second contact portion at a further tissue region, wherein a mechanical oscillation generator is arranged between the implant parts, and FIG. 7 schematically shows the implant of FIG. 6 in a deflected position.

DETAILED DESCRIPTION OF THE INVENTION

The following description is of the best mode presently contemplated for carrying out at least one embodiment of the invention. This description is not to be taken in a limiting sense, but is made merely for the purpose of describing the general principles of the invention. The scope of the invention should be determined with reference to the claims.

One or more embodiments of the invention are described on the basis of epicardial pacemakers. In at least one embodiment, however, other permanently implantable electronic implants for diagnostics and/or therapy that may be inserted between body tissue regions that perform a relative movement with respect to one another may be used.

Figure 2:
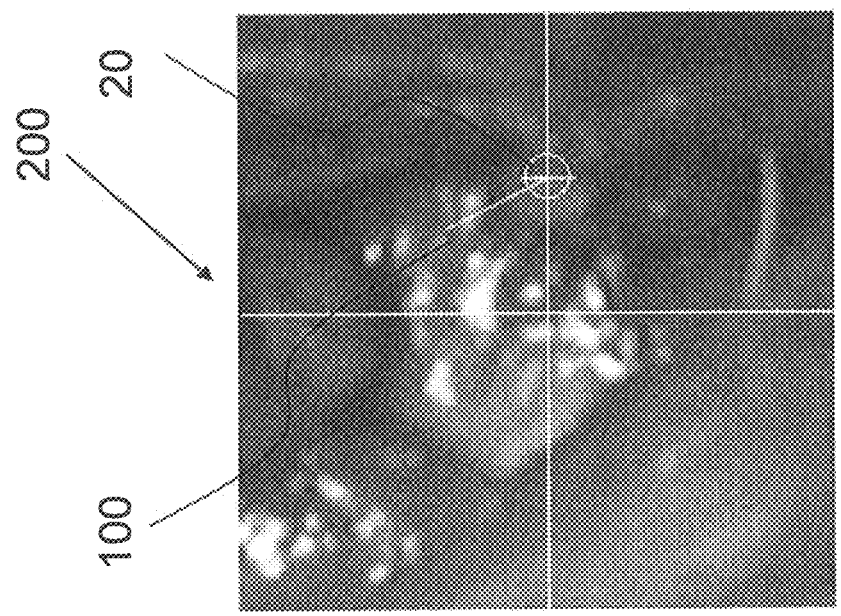
FIG. 2 shows relative movements present between myocardium and pericardium with an epicardial implant with a tissue region in a second position compared with FIG. 1.
Figure 1:
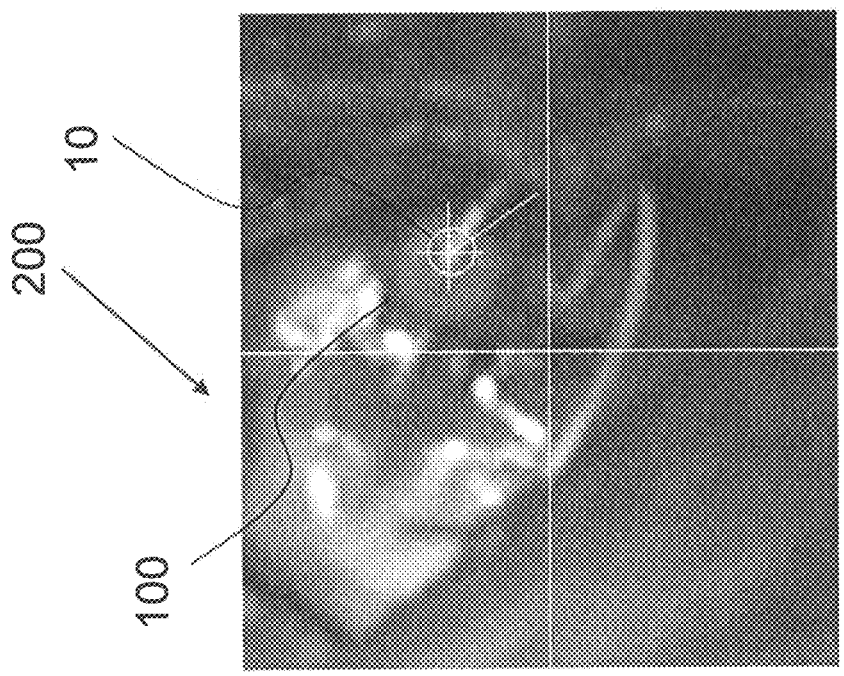
FIG. 1 shows relative movements present between myocardium and pericardium with an epicardial implant with a tissue region in a first position.

FIGS. 1 and 2 illustrate relative movements present between two tissue regions of the myocardium and pericardium in an implantation area 200 in which an epicardial implant 100 is inserted, according to one or more embodiments of the invention. By way of at least one embodiment, FIG. 1 shows the implantation area 200 with a tissue region in a first position 10. According to one or more embodiments, FIG. 2 shows a tissue region in a second position 20. In at least one embodiment, the relative movement of the tissue between the two positions 10, 20 may be used to generate electrical energy in the implant 100. In one or more embodiments, the path covered from the first position 10 relative to the furthest position 20 may be approximately 10 mm. In at least one embodiment, the movement may be caused by a muscular force that may then be diverted accordingly to sufficiently recover energy.

Figure 3:
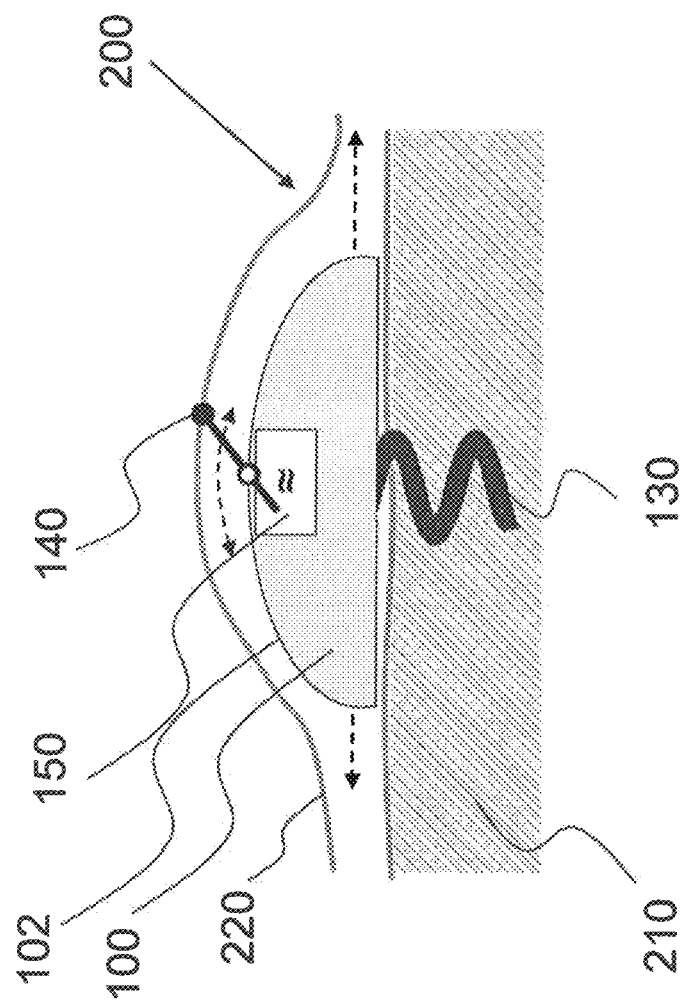
FIG. 3 schematically shows a section through an implantation area with an epicardial implant according to an exemplary embodiment of the invention, which is fixed via a first contact portion in the form of a fixing helix in a first tissue region and which is fixed via a second contact portion at a further tissue region.

FIG. 3 shows a section through an implantation area 200 with an epicardial implant 100 according to one or more embodiments of the invention. In at least one embodiment, the implant 100 may include an implant housing 102, which is fixed via a first contact portion 130 in the form of a fixing helix in a first tissue region 210, for example the myocardium, and which is fixed via a second contact portion 140 to an opposed further tissue region 220, for example the pericardium. In one or more embodiments, the second contact portion 140 may be coupled directly to an electric generator 150 in the implant body 102 and may move a magnet of the generator 150 relative to a coil (not illustrated) when the tissue regions 210, 220 perform a movement relative to one another. In at least one embodiment, the second contact portion 140 may be movably mounted and may perform a tilting movement about a hinge joint.

In one or more embodiments of the invention, a lateral relative movement between the two tissue regions 210, 220 may be predefined in the implantation area 200 and is indicated in FIG. 3 by dashed arrows pointing to the right and left. In at least one embodiment, the two contact portions 130, 140 may be connected to their respective tissue region 210, 220 and may be entrained thereby, such that the second contact portion 140 entrains the magnet of the generator 150 via a mechanical coupling when the contact portion 140 performs its tilting movement. In one or more embodiments, the contact portion 140, for example, may be adhesively bonded to the tissue region 220, for example using a fibrin adhesive or another suitable adhesive.

By way of at least one embodiment, the magnet may be electromagnetically operatively connected to the coil and induces an electric voltage in the coil, which may be used to operate the implant 100, for example for diagnosis delivery. In one or more embodiments, the electrical energy may be stored in an electric store (not illustrated) and called up as necessary. In at least one embodiment, the coil may be moved relative to the magnet.

FIGS. 4 and 5 show a section through an implantation area 200 with an epicardial implant 100 according to one or more embodiments of the invention. In at least one embodiment, the implant may be divided into two. FIG. 4 shows the epicardial implant 100 in a first position, whereas FIG. 5 shows the implant 100 from FIG. 4 in a deflected position.

In one or more embodiments, a first part 110 of the implant 100 may be fixed via its first contact portion 130 in the form of a fixing helix in a first tissue region 210, for example the myocardium, and a second part 120 of the implant 100 may be fixed via its second contact portion 140 to a further tissue region 220, for example the pericardium. In at least one embodiment, the parts 110, 120 may be connected via a resilient compound, in which strip-like piezoelectric elements 170 are embedded and may form a generator. In one or more embodiments, the second contact portion 140 may be fixed, for example as a barb, in the second tissue region 220.

According to at least one embodiment, when the tissue regions 210, 220 perform a lateral movement relative to one another, as is indicated in FIG. 5 by dashed arrows pointing to the right and left, the piezoelectric elements 170 may be deformed. In one or more embodiments, the piezoelectric elements 170 may induce an electric voltage, which may serve as a voltage source for a current delivery, and/or may be coupled to an energy store 180, for example an electrochemical energy store, to store energy.

FIGS. 6 and 7 show a section through an implantation area 200 with an epicardial implant 100 according to one or more embodiments of the invention. In at least one embodiment, the implant may be divided into two. FIG. 6 shows the epicardial implant 100 in a first position, and FIG. 7 shows the implant 100 from FIG. 6 in a deflected position.

By way of one or more embodiments, a first part 110 of the implant 100 may be fixed via a first contact portion 130 in the form of a fixing helix in a first tissue region 210, for example the myocardium, and a second part 120 of the implant 100 may be fixed via a second contact portion 140 in the form of a bar to a further tissue region 220, for example the pericardium. At least one embodiment of the invention may include a generator 150 in the form of a micromechanical electrostatic generator 410 arranged in the second implant part 120. In one or more embodiments, electrostatic generators may include microelectromechanical system (MEMS) resonators, which may be excited via vibration energy. In at least one embodiment, MEMS resonators may generate approximately 150 $\mu W/cm^2$ at their active chip face with suitable excitation, which is sufficient to supply to a pacemaker system. In one or more embodiments, the "high-performance electrostatic MEMS vibration energy harvesters" may generate their maximum power with suitable mechanical excitation, frequency and pulse shape. In at least one embodiment, a mechanical oscillation generator 420, for example a frictional surface, may be provided between the first and second part 110, 120 of the implant 100. In one or more embodiments, when the expected relative movement is performed, the mechanical oscillation generator 420 may generate a matching excitation frequency in the part 120 with the micromechanical electrostatic generator 410.

In at least one embodiment, the generator 150, 410 may be arranged on an accordingly matched resonator (not illustrated).

One or more embodiments of the invention may include a control and/or regulation unit (not illustrated in the Figures) in the implant body 102, or a control and/or regulation unit that may be coupled thereto, to induce a therapeutic energy delivery. As such, in at least one embodiment, energy may be used that is stored in a corresponding energy store 180 in the implant 100. In one or more embodiments, a control and/or regulation unit may include an electronic circuit that initiates or stops or varies the corresponding therapy in accordance with the therapeutic demand, for example a timer in a cardiac pacemaker.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

What is claimed is:

1. A medical implant for insertion into the human and/or animal body, comprising:
    an implant body, wherein the implant body comprises at least one first and at least one second contact portion;
    wherein the at least one first and the at least one second contact portions are configured to contact two tissue regions performing a relative movement with respect to one another,
    wherein the at least one first and the at least one second contact portions are movable relative to one another, and a relative movement of the at least one first and the at least one second contact portions is converted into electrical energy,
    wherein one or more of the at least one first contact portion and the at least one second contact portion is coupled directly or indirectly to an electric generator in or on the implant body,
    wherein the electric generator comprises a magnet and a coil,
    wherein the at least one second contact portion is coupled directly to the electric generator and moves the magnet of the electric generator relative to the coil when the two tissue regions move relative to one another,
    wherein the magnet moves laterally relative to the coil when the two tissue regions move laterally relative to one another as a lateral relative movement,
    wherein the magnet is electromagnetically connected to the coil and induces an electric voltage in the coil to operate the medical implant,
    wherein the implant body further comprises an electric store, and,
    wherein the electrical energy is stored in the electric store and called up as necessary.

2. The medical implant as claimed in claim 1, wherein the at least one first contact portion comprises a fixing element to fasten the implant body to one of the two tissue regions.

3. The medical implant as claimed in claim 1, wherein one or more of the at least one first contact portion and the at least one second contact portion is mechanically connected to a movable element of the electric generator provided in or on the implant body.

4. The medical implant as claimed in claim 1, wherein the implant body comprises a number of parts, wherein at least two parts of the number of parts are movable relative to one another and each of the number of parts of the implant body is associated with a contact portion.

5. The medical implant as claimed in claim 4, wherein the number of parts are coupled using at least one piezoelectric element.

6. The medical implant as claimed in claim 4, further comprising a mechanical oscillation generator arranged between the number of parts of the implant body.

7. The medical implant as claimed in claim 1, wherein the electric generator is an electrostatic generator, and wherein the electric generator is driven via mechanical waves.

8. The medical implant as claimed in claim 4, wherein the at least one second contact portion comprises a fixing element to fasten the implant body to one of the two tissue regions.

9. The medical implant as claimed in claim 1, further comprising a control and/or regulation unit, wherein the control and/or regulation unit is in the implant body or is coupled thereto to induce a therapeutic energy delivery.

10. The medical implant as claimed in claim 1, wherein the implant comprises an epicardial pacemaker.

11. The medical implant as claimed in claim 6, wherein when an expected relative movement is performed, the mechanical oscillation generator generates a matching excitation frequency in a second part of the at least two parts with the electric generator.

12. The medical implant as claimed in claim 1, wherein the at least one second contact portion is moveably mounted and performs a titling movement about a hinge joint, wherein the lateral relative movement between the two tissue regions is predefined, such that the at least one first contact portion and the at least one second contact portion are connected to their respective tissue regions of the two tissue regions, and such that the at least one second contact portion entrains the magnet via a mechanical coupling when the at least one contact portion performs the tilting movement.

* * * * *